United States Patent [19]

Son et al.

[11] Patent Number: 4,841,053
[45] Date of Patent: Jun. 20, 1989

[54] PROCESS FOR DESENSITIZING A 1-(ALKYLAMINO)ALKYL-POLYSUBSTITUTED PIPERAZINONE DURING RECOVERY

[75] Inventors: Pyong-Nae Son, Akron; Charles P. Jacobs, Elyria; Ronald M. Kovach, Avon Lake; John T. Lai, Broadview Heights, all of Ohio

[73] Assignee: The B. F. Goodrich Company, Akron, Ohio

[21] Appl. No.: 146,532

[22] Filed: Jan. 21, 1988

Related U.S. Application Data

[63] Continuation-in-part of Ser. No. 848,555, Apr. 7, 1986, abandoned.

[51] Int. Cl.$^4$ ............................................. C07D 241/08
[52] U.S. Cl. ..................................... 544/384; 544/231; 544/360
[58] Field of Search ........................ 544/231, 360, 384

[56] References Cited

U.S. PATENT DOCUMENTS

| | | | |
|---|---|---|---|
| 4,167,512 | 9/1979 | Lai | 544/384 |
| 4,190,751 | 2/1980 | Lai et al. | 544/384 |
| 4,466,915 | 8/1984 | Lai | 544/384 |
| 4,780,495 | 10/1988 | Lai et al. | 544/384 |

*Primary Examiner*—Richard L. Raymond
*Assistant Examiner*—James H. Turnipseed
*Attorney, Agent, or Firm*—Alfred D. Lobo; Nestor W. Shust

[57] ABSTRACT

Certain polysubstituted piperazinones (PSP) having two or three methylene groups linking the $N^1$ atom of the ring to the N atom of a terminal amine group, are found to be peculiarly prone to decomposition when subjected to elevated temperature after being contacted with water, and sensitive to the amount of base used in the base-induced ketoform reaction which generates the PSP represented by the structure

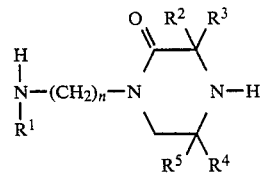

These PSP are therefore produced by a modification of the ketoform reaction under essentially anhydrous conditions, using enough ketone to dissolve the PSP formed and a molar ratio of solid alkali metal hydroxide/diamine reactant in the range from at least 5 but less than 7. The PSP produced is recovered as a solution in the ketone, without contacting the PSP with water. The PSP product obtained after the ketone is distilled, is essentially pure.

5 Claims, No Drawings

PROCESS FOR DESENSITIZING A 1-(ALKYLAMINO)ALKYL-POLYSUBSTITUTED PIPERAZINONE DURING RECOVERY

CROSS-REFERENCE TO RELATED APPLICATION

This application is a continuation-in-part application of Ser. No. 848,555 filed Apr. 7, 1986 now abandoned.

BACKGROUND OF THE INVENTION

Polysubstituted piperazinones ("PSP" for brevity) are well known stabilizers for synthetic resinous materials exposed to environmental degradation and ultraviolet (uv) light, in particular. Such materials are disclosed in U.S. Pat. Nos. 4,167,512; 4,190,571; 4,240,961; 4,292,240; 4,297,497; 4,466,915; and 4,480,092, inter alia. The commercial process for the manufacture of the PSPs is by the non-catalytic base-induced ketoform synthesis described in U.S. Pat. No. 4,466,915 patent, the disclosure of which is incorporated by reference thereto as if fully set forth herein.

This invention derives from the discovery that particular 1-(alkylamino)alkyl-PSPs having 2 or 3 ($CH_2$) groups connecting the $N^1$ of the diazacycloalkane ring to the N atom of the terminal amine group, are peculiarly prone to decomposition of subjected to elevated temperatures in the range in which the ketone (from which the PSP is derived) boils, hence termed "water-sensitive". This water-sensitivity is particularly evident when such PSPs are contacted with large amounts of water. Therefore the invention relates to the recovery by distillation of a PSP from an essentially anhydrous reaction mass without using water in any step during synthesis of, or, recovery of the product.

U.S. Pat. No. 4,299,497 reference states "The preferred alkali is an aqueous alkali metal hydroxide solution such as aqueous sodium hydroxide, or potassium hydroxide, preferably in the range from about 20 percent to 70 percent solutions. If the alkali metal hydroxide is used in solid form, it is preferably in finely divided form typically less than 80 U.S. Standard mesh in size. The amount used is not critical but at least a trace amount appears to be essential for the progress of the desired reaction. It is preferred to use sufficient aqueous alkali solution to form a visually distinct aqueous phase in the presence of the organic solvent phase. In general, the amount of aqueous alkali used is preferably at least 5 percent by weight of the reaction mass. There is no advantage to using more aqueous alkali than about 75 percent by weight of the reaction mass." (col 11, lines 33–48).

The synthesis was illustrated in U.S. Pat. No. 4,297,497 in examples which required the addition of a phase transfer catalyst (BTAC) because at the time, that was the only way to run the reaction. Specifically, with respect to addition of the alkali, I stated in example 3 ".. 40 ml conc NaOH (50 % by wt) is dripped into the flask over about 30 mins. The reaction is allowed to proceed for about 5 hr.." (see col 13, lines 14–16). In another example (6) Lai stated "Then add 40 l conc NaOH (50 % by wt) to the reaction mixture dropwise, so the temperature does not exceed 30° C." (see col 14, lines 23–26). The slow addition of NaOH is necessary because it is the exotherm-controlling step. Addition of the alkali in solid, finely divided particulate form, allowed better control of the rate of reaction. Because it was a phase transfer catalyzed reaction, one could add a large excess of alkali without adverse side effects, namely production of undesirable byproducts of side reactions. The addition of a very large excess of alkali in a non-catalytic synthesis, is in a different reaction environment, distinguishable because of the absence of the phase transfer catalyst, and is the nexus of the conventional (original) commercialization of the non-catalytic synthesis, and the present invention.

Briefly, the ketoform synthesis comprises reacting a N,N'-alkyl substituted ethylene diamine with an acyclic or cyclic ketone, and chloroform, in the presence of aqueous or solid alkali, and, a large excess of ketone, in the presence of a phase transfer catalyst, as described in the 4,167,512 patent issued Sept. 11, 1979, more fully in U.S. Pat. No. 4,297,497 pat. issued Oct. 27, 1981, the disclosures closures of which are incorporated by reference thereto as if fully set forth herein. Three years later, Lai described how to run the reaction without a catalyst in U.S. Pat. No. 4,466,915 pat., issued Aug. 21, 1984; and, about the same time how to use solid NaOH in a solvent (say, toluene) to function as an HCl acceptor to couple one or more PSP moieties to a triazine nucleus (by reaction of cyanuric chloride with the PSP) in U.S. Pat. No. 4,480,092, issued Oct. 30, 1984. U.S. Pat. No. 4,466,915 titled "Non-Catalytic Ketoform Synthesis" provides all relevant facts known about the prior art process as they relate to its commercialization in a conventional non-catalytic ketoform synthesis.

The ketoform reaction which generates the PSP by cyclizing the N,N'-alkyl substituted ethylene (or propylene) diamine, depends upon the generation of a $CCl_3$ anion provided by the action of NaOH on chloroform. This aniongenerating function of the NaOH is provided by aqueous or solid alkali, in the presence of the phase transfer catalyst, and also when there is no catalyst present. In the reaction which uses solid NaOH to couple the PSP formed by the ketoform reaction with a triazine, the NaOH performs the function of a Hcl acceptor, allowing the PSP is displaced. The formation of HCl is unrelated to the formation of any ion. Both these reactions are taught in U.S. Pat. No. 4,480,092. In all illustrative examples which teach the formations of the PSP, aqueous sodium hydroxide was used because U.S. Pat. No. 4,480,092 referred to U.S. Pat. No. 4,167,512 (see col 11, line 43) which was the catalytic synthesis. No mention is made about the effect of a large excess of solid NaOH is the PSP synthesis because of the particular amount of the excess was not deemed critical. U.S. Pat. No. 4,167,512 patent taught a range from 5 percent to 75 percent by weight of the reaction mass (see btm of col 10).

On the other hand, U.S. Pat. No. 4,466,915 patent which deals with the non-catalytic synthesis, clearly spelled out the criticality of the excess of alkali (whether aqueous or not). It states "It is preferred to use sufficient aqueous alkali solution to form a visually distinct aqueous phase in the presence of the organic solvent phase. In general, the amount of aqueous alkali used is preferably about three (3) equivalents of the amine. A slight excess over three equivalent (sic) is preferable, but a large excess is to be avoided.

Through aqueous alkali is most preferable, water is not an essential requirement for the progress of the synthesis, though it will be appreciated that even where solid alkali metal hydroxide is used, there may be a trace of water associated with it." (see col 4, lines 53–63).

In all the references relating to the recovery of PSPs we used a water-imiscible chlorocarbon such as chloroform or methylene chloride in which most PSPs are preferentially soluble relative to their solubility in a ketone, to extract the PSP from the reaction mass. Since many of the PSPs formed were not substantially soluble in the ketone used as a reactant, were not known to be sensitive to being contacted with copious quantities of water, and were partly precipitated with the salt (NaCl, if NaOH was used), extraction with the chlorocarbon was a most convenient and effective way of extracting the PSP from the reaction mass. However since much of the ketone and some of the salt was extracted in the chlorocarbon, we used water to wash out the remaining ketone, and also the salt formed during the ketoform reaction. Since these references were to 1,4-PSPs in general, the sensitivity of PSPs with the 2 or 3 methylene group linkage, to water, was not known, and therefore never a consideration.

It was in the framework of the foregoing facts that we happened to find that a large excess of alkali, at least five moles for each mole of amine reactant used to produce the desired water-sensitive PSP, in a large excess of essentially anhydrous ketone, sufficient to completely dissolve the PSP formed, avoided the use of a chlorocarbon solvent and a water wash. Because this PSP was never contacted with water, this method desensitized the PSP's proclivity to degradation during the distillation steps required for its workup and recovery.

SUMMARY OF THE INVENTION

It has been discovered that the ketoform synthesis may be modified to prepare water-senstive polysubstituted piperazinones (PSP) which are peculiarly prone to decomposition when subjected to elevated temperatures after being contacted with water, provided (i) they are substantially completely soluble in the ketone used to produce them, (ii) if at least 5 mols of solid alkali metal hydroxide for each mol of triamine reactant are used, and (iii) the PSP reaction product is not contacted with water during its purification and recovery. By "substantially completely soluble" we refer to a PSP which has a solubility of at least 20 gm per 100 gm of ketone from which it is derived.

It is therefore a general object of this invention to provide a suprisingly effective yet simple modification of a known process for preparing a PSP from a triamine which is an acyclic or cyclic N-substituted-1,2 diamine or 1,3-diamine, comprising, contacting said triamine with a saturated acyclic or cyclic monoketone present in an amount from about 2 to about 25 times greater than the molar amount required to react with said triamine, in the absence of a phase transfer catalyst and a primary alcohol solvent, and in the presence of a base and sufficient haloform to produce the PSP at a temperature in the range from above the freezing point of the reaction mass up to about the reflux temperature thereof, which process requires extracting the PSP from the reaction mass with a chlorocarbon and washing the chlorocarbon with water to remove undesirable water-soluble reaction products, the ketone and salt, and removing the ketone and chlorocarbon so as to recover a substantially pure PSP.

The modification comprises, (i) adding a large excess of solid alkali metal hydroxide, more than five moles for each mole of said triamine, as a reactant to provide an anion-generating function in a sufficiently large quantity of substantially water-free keton in which the PSP is substantially completely soluble, (ii) producing the water-sensitive PSP which forms a PSP-ketone solution, the PSP being represented by the structure

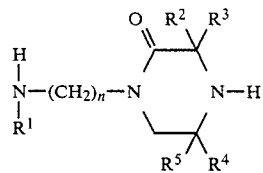

wherein, n represents 2 or 3, bing the number of methylene groups linking the terminal amino group to the $N^1$ atom of the piperazinone, $R^1$ represents $C_1$–$C_{12}$ alkyl, $C_5$–$C_{12}$ cycloalkyl, phenyl, napthyl, alkylphenyl and alkyl-naphthyl each alkyl substituent being $C_1$–$C_{12}$, and, $R^2$, $R_3$, $R^4$, and $R^5$ each represent $C_1$–$C_{12}$ alkyl, $C_1$–$C_8$ hydroxyalkyl, $C_1$–$C_8$ aminoalkyl, $C_1$–$C_8$ alkoxyalkyl, and, $C_5$–$C_{12}$ cycloalkyl, and in combination, $R^2$ with $R^3$, and $R^4$ with $R^5$, represent $C_5$–$C_{14}$ cycloalkyl having at least four of the C atoms cyclized;

(iii) separating an essentially anhydrous PSP-ketone solution substantially free of a salt of said alkali metal, without contacting said solution with water; and, (iv) distilling low-boiling byproducts and said ketone from said solution and recovering the PSP in essentially pure form without degrading it.

DETAILED DESCRIPTION OF A PREFERRED EMBODIMENT

It is evident that the need to devise an essentially water-free process for producing a substantially pure polysubstituted piperazin-2-one (PSP) arose from the discovery; quite by chance, that PSPs with two or three methylene groups in the linkage connecting the $N^1$ atom of the PSP ring to the N atom of the terminal amino group, were prone to be degraded during distillation steps used to recover them, because of their water-sensitivity.

It appears that the other substituents on the PSP do not contribute to water-sensitivity of the PSP, and therefore are not narrowly critical. For practical reasons, $R^1$ on the terminal amino group is preferably selected from alkyl having from 1 to about 12 carbon atoms ($C_1$–$C_{12}$ alkyl) ranging from methyl to n-dodecyl, more preferably lower $C_1$–$C_6$ alkyl, particularly methyl, ethyl, propyl, n-butyl, isobutyl and n-hexyl, $C_5$–$C_{12}$ cycloalkyl, and phenyl each of which may have lower alkyl substituents.

For similar reasons, it is preferred that $R^2$, $R^3$, $R^4$, and $R^5$, be $C_1$–$C_{12}$ alkyl, and as before, more preferably lower $C_1$–$C_6$ alkyl. Cyclic substituents are preferably cycloalkylene spiro substituents such as pentamethylene and hexamethylene, which may have lower alkyl substituents, piperidyl, and polysubstituted piperidyl, for example, 2,2,6,6-tetramethylpiperidyl.

Examples of water-sensitive 1-(alkylamino)alkyl-2-keto-1,4-diazacrycloalkanes referred to herein as polysubstituted piperazinones (PSP) are:

1-[2-butylamino)ethyl]-3,3,5,5-tetramethyl-2-piperazinone;

1-[2-(isopropylamino)ethyl]-3,3,5,5-tetramethyl-2-piperazinone;

1-[2-(1,3-dimethylbutylamino)ethyl]-3,3,5,5-tetramethyl-2-piperazinone;

1-[2-(cyclohexylamino)ethyl]-3,3,5,5-tetramethyl-2-piperazinone;

1-[2-(cyclooctylamino)ethyl]-3,3,5,5-tetramethyl-2-piperazinone;

1-[2-(cyclododecylamino)ethyl]-3,3,5,5-tetramethyl-2-piperazinone;

1-[2-methylheptylamino)ethyl]-3,3,5,5-tetramethyl-2-piperazinone;

1-[2-(cyclohexylamino)propyl]-3,3,5,5-tetramethyl-2-piperazinone;

1-[3-methylamino)propyl))-3,3,5,5-tetramethyl-2-piperazinone;

1-[3-(cyclohexylamino)propyl]-3,3,5,5-tetramethyl-2-pipereazinone; and,

1-[3-cyclododecylamino)propyl]-3,3,5,5-tetramethyl-2-piperazinone.

It will be evident that the critical 2 or 3 methylene group linkage will be provided by a triamine N-substituted-1,2-or 1,3-diamone) which functions as a nucleophilic agent in this base-induced non-catalytic ketoform synthesis. The diamine may be primary or a secondary amine and will have the appropriate structure to provide the desired substituents in the cyclized PSP. A straight chain or acyclic triamine will be appropriate where the PSP is to be formed, and a cyclic triamine will be used when a PSP with spiro substituents is desired.

Because the haloform is a necessary reactant, it is present in at least an equimolar amount as the amine, and in practice, a slight excess up to about 50% over stoichemitric is used to minimize the formation of unwanted byproducts. Either chloroform or bromoform may be used, but chloroform is preferred, both for efficient reactivity and economy.

It will be evident that the choice of the ketone will be determined by the desired substituents on the PSP at the 3-carbon position, because, in addition to be instrumental in providing the two-carbon bridge carrying the oxygen atom, the ketone provides these substituents at the 3-C atom. The amount of the ketone used is in large excess sufficient to dissolve substantially all the PSP produced, so that, upon filtration, the PSP product leaves as a PSP-ketone solution. Since most monoketones used do not dissolve a significant amount of the alkali metal halide salt (usually NaCl because NaOH is used) formed during the reaction, the salt is left in the reaction mass as a precipitate which is readily separated by filtration.

The preferred base for inducing the reaction, is solid sodium hydroxide or potassium hydroxide, as a finely divided powder, or as beads, typically smaller than 20 U.S. Standard mesh size, either of which is commercially availble. Though it was previously determined that the alkali was preferably present in an amount slightly in excess over three equivalents (of the amine) theoretically required to cyclize all the amine nucleophilic agent, a water-sensitive PSP so formed is subject to an unacceptably high level of degradation during its recovery by distillation, even if it is not contacted with water. But increasing the amount of alkali in the range from 5 to 6 mols per mol of diamine, inexplicably circumvents the problem.

Because the alkali sets off the reaction, the triamine (i.e. N-substituted diamine), ketone and chloroform are charged to a jacketed, cooled reactor and mixed before the alkali is added to the mixture maintained at about 0° C by controlling the exotherm so that the reaction temperature does not exceed about 10° C.

Commercially available reactants are used, and the ketones in particular, for example acetone, 2-butanone and cyclohexanone may contain a trace of water not enough to produce an unacceptable level of degradation. The amount of water contamination which may be tolerated can be arrived at by simple trial and error, by deliberately adding a small known, amount of water to determine at what point it produces objectionable degradation.

The reaction proceeds at ambient pressure, and pressure, whether superatmospheric or subatmospheric, is not a critical consideration. Atmospheric pressure is preferred because there appears to be no significant economic advantage to be gained from operating at either higher or lower pressures.

The reaction mass, upon completion of the reaction, is typically a slurry in which the PSP is present as a PSP-ketone solution, and the salt (NaCl) is precipitated. It is of particular significance, and wholly unpredictable, that so little of the salt would be dissolved in the PSP-ketone solution that no additional step for removal of the salt is necessary to purify the PSP. Purification of the filtrate may be accomplished in a single step by simple distillation, preferably under reduced pressure.

Degradation of the PSP may be detected, if severe, by visually observing a smoky vapor in the distillation column during distillation, or, for less severe degradation, by any of several analytical techniques, most conveniently by gas chromatographic (GC) analysis.

For reasons not understood at the present time, the degradation of water-sensitive PSPs is critically sensitive to the amount of alkali present during the ketoform reaction. As will presently be demonstrated in illustrative examples, objectionable degradation occurs when the concentration of alkali is less than 5 mols per mol of triamine, but is not noticeable when the concentration is in the range from 5 to 6 mols of alkali per mol of triamine. Also remarkable is that, despite the objectionable level of undesirable byproducts produced when the concentration of alkali exceeds about 7 mols/mol of triamine, the same very high concentration of alkali in the distillation column appears to provide added protection against objectionable degradation.

In the following examples, a particular water-sensitive PSP is produced by the process of U.S. Pat. No. 4,466,915 patent, involving extracting with a hydrochloromethylene and washing with water (example 1); and, for comparison, by the process of this invention, with no water contact (example 2); though, in each case, solid NaOH is used in the noncatalytic ketoform process. In the subsequent examples, the same PSP is produced with a molar ratio of NaOH to triamine of 5.0 (example 3); and, for comparison, with a molar ratio of 7 (example 4); in each case, without contact with water.

EXAMPLE 1

Preparation of 1-[3-cyclohexylamino)propyl]-3,3,5,5-tetramethyl-2-piperazinone represented by the structure:

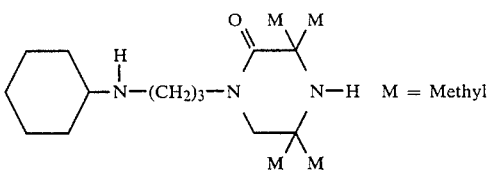

A 5-liter, 3-necked flask in an ice-bath is charged with 1833 ml (24.9 mols) of acetone, and 230 ml (2.88 mols) of chloroform which are mixed and cooled to a temperature of about 6° C. Both reactants are commercially pure and used as taken from 55 gal barrels in which they were delivered. An analysis showed that the acetone was contaminated with about 200 ppm of water. To obtain a molar ratio of acetone/diamine of about 13, 562.4 gm (1.92 mols) of N'-[3-(cyclohehxylamino)-propyl]-2-methyl-1,2-propanediamine are added, mixed with the charge in the flask, and cooled to 4° C. Then a first addition of 2.5 gm of NaOH beads to the charge initiates an exothermic reaction the temperature of which is controlled in the range from about −5° C. to 10° C.; a few minutes later, more NaOH beads are incrementally introduced into the reaction mass over a period of several (about 4) hours until a total of 399.4 gm (9.98 mols) of NaOH are added to the flask, so that the molar ratio of NaOH to diamine is 5.2, and the reaction is subsequently allowed to proceed to completion over a period of about 2 hr while the reaction temperature was maintained in the above-designated range.

The reaction mass is a slurry which is thoroughly mixed with 1500 ml of water to extract the NaCl and other water-soluble byproducts, and the organic and water phases of the mixture allowed to settle so that the organic phase may be decanted. The water phase is discarded.

The organic phase is distilled in a glass distillation column, preferably in stages, first to remove some of the acetone with unwanted byproducts which boil at a lower temperature (referred to as "low-boils") than the PSP, then the remaining acetone and chloroform fractions, to leave the PSP. A smoke-grey vapor is seen indicating decomposition which is comfirmed by a GC analysis of the residue. The purity of the residue is less than 80%, the contaminants being a variety of low boiling byproducts attributable to the water-sensitivity of the PSP.

EXAMPLE 2

The PSP produced in example 1 hereinabove is prepared in an analogous manner using the same commercially available reactants in the same molar ratio, namely, acetone/diamine =13, and NaOH/diamine =5.2, and the same amount of chloroform (230 ml, or 2.88 mols) again adding the NaOH beads incrementally so as to maintain the reaction temperature in the above-designated range. The reaction mass obtained as a slurry is filtered and the cake washed with enough acetone to dissolve and remove any PSP which is dispersed within the mass of predominantly NaCl crystals. The solution of PSP in acetone is then distilled in the glass distillation column, preferably in stages, as before, to remove the low-boils and some acetone, then the remaining acetone, to purify the PSP. The distillation proceeds with no visible evidence of a smoke-grey vapor. A GC analysis of the purified PSP, after fractionation of the low-boils, shows that the PSP is from 97% to nearly 100% pure.

EXAMPLE 3

The PSP produced in example 2 hereinabove is prepared in an analogous manner using the same commercially available acetone, chloroform and triamine, with the molar ratio of acetone/diamine =13, and the same amount of chloroform, except that 384.2 gm (9.6 mols) of NaOH beads are used, so that the molar ratio of NaOH/diamine =4.9. Again, the NaOH beads are added incrementally so as to maintain the reaction temperature in th above-designated range. As before, the slurry obtained is filtered, and the cake washed with enough acetone to dissolve remaining PSP in the cake. The solution of PSP in acetone is then distilled as in example 2 hereinabove to purify the PSP. There is visible evidence of a smoke-grey vapor as the distillation proceeds. A GC analysis of the residue shows the PSP is less than 78% pure.

EXAMPLE 4

The PSP produced in example 3 hereinabove is prepared in an analogous manner except that 548.8 gm (13.7 mols) of NaOH beads are used, so that the molar ratio of NaOH/triamine =7. Again, the NaOH beads are added incrementally so as to maintain the reaction temperature in the above-designated range. As before, the slurry obtained is filtered, and the cake washed with enough acetone to dissolve remaining PSP in the cake. The solution of PSP in acetone is then distilled as in example 3 hereinabove to purify the PSP. There is no visible evidence of a smoke-grey vapor as the distillation proceeds but a GC analysis of the residue shows the PSP is less than 80% pure.

From the foregoing comparative examples it is evident that not only is it critical that the reaction be carried out under substantially anhydrous conditions, without allowing the PSP produced to be contacted with water during any stage of its purification, but the molar ratio of alkali to diamine must be in the range from more than 5 but below 7, and therefore is also critical.

We claim:

1. In a process for preparing a polysubstituted piperazinone reaction product from a triamine which is an acyclic or cyclic N-substituted-1,2-diamine or 1,3-diamine, comprising, contacting said triamine with a saturated acyclic or cyclic monoketone present in an amount from about 2 to about 25 times greater than the molar amount required to react with said triamine, in the absence of a phase transfer catalyst and a primary alcohol solvent, and in the presence of an alkali metal hydroxide and sufficient haloform to produce said reaction product at a reaction temperature in the rnage from above the freezing point of the reaction mass, up to about the reflux temperature thereof, and recovering said polysubstituted piperzinone, the improvement consisting essentially of (i) adding a large excess of solid alkali metal hydroxide, at least five moles for each mole of said triamine, (ii) producing a substantially completely monoketonesoluble water-sensitive polysubstituted piperazin-2-one represented by the structure

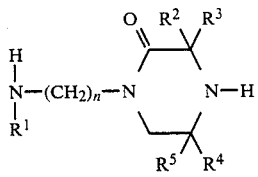

wherein, n represents 2 or 3, being the number of methylene groups linking the terminal amino group to the $N^1$ atom of the piperazinone, $R^1$ represents $C_1$–$C_{12}$ alkyl, $C_5$–$C_{12}$ cycloalkyl, phenyl, naphthyl, alkylphenyl and alkyl-napahthyl each alkyl substituent being $C_1$–$C_{12}$, and, $R^2$, $R^3$, $R^4$, and $R^5$ each represent $C_1$–$C_{12}$ alkyl, $C_1$–$C_8$ hydroxylaklyl, $C_1$–$C_8$ aminoalkyl, $C_1$–$C_8$ alkoxylakyl, and, $C_5$–$C_{12}$ cycloalkyl, and in combination, $R^2$ with $R^3$, and $R^4$ with $R^5$, represent $C_5$–$C_{14}$ cycloalkyl having at least four of the C atoms cyclized;

(iii) separating an essentially anhydrous solution of said polysubstituted piperazinone in said monoketone substantially free of a salt of said alkali metal, without contacting said solution with water; and, (iv) distilling unwanted low-boiling byproducts and said ketone from said solution to purify said polysubstituted piperazinone without degrading it.

2. The process of claim 1 wherein said alkali metal hydroxide is selected from the group consisting of sodium hydroxide and potassium hydroxide present as a finely divided solid.

3. The process of claim 2 wherein said large excess of said alkali metal hydroxide is in the range from 5 to about 6 moles per mole of said diamine.

4. The process of claim 3 wherein said haloform is selected from the group consisting of chloroform and bromoform.

5. The process of claim 4 wherein said temperature is in the range from about −10° C. to about 10° C.

* * * * *